United States Patent
Samarasekera et al.

[11] Patent Number: 5,960,055
[45] Date of Patent: Sep. 28, 1999

[54] FAST CONE BEAM IMAGE RECONSTRUCTION USING A DETECTOR WEIGHT LIST

[75] Inventors: Supun Samarasekera; Frank Sauer, both of Princeton; Kwok Tam, Edison, all of N.J.

[73] Assignee: Siemens Corporate Research, Inc., Princeton, N.J.

[21] Appl. No.: 08/994,605

[22] Filed: Dec. 19, 1997

[51] Int. Cl.⁶ .................................................. A61B 6/03
[52] U.S. Cl. .............................................. 378/4; 378/901
[58] Field of Search .......................... 378/4, 15, 901; 382/131

[56] References Cited

U.S. PATENT DOCUMENTS

| | | | |
|---|---|---|---|
| 5,640,436 | 6/1997 | Kawai et al. | 378/4 |
| 5,862,198 | 1/1999 | Samarasekera et al. | 378/4 |
| 5,901,195 | 5/1999 | Sauer et al. | 378/4 |
| 5,901,196 | 5/1999 | Sauer et al. | 378/4 |

*Primary Examiner*—David Vernon Bruce
*Attorney, Agent, or Firm*—Lawrence C. Edelman

[57] ABSTRACT

A method and apparatus are provided for three dimensional computerized tomographic imaging of an object, wherein cone beam energy from a cone beam source is applied to at least a portion of an object to be imaged by causing relative rotational motion between the source and the object at a plurality of source positions along a path scanning trajectory. An area detector receives cone beam energy from the source on a plurality of detector elements arranged in an array of rows and columns, so that its detector elements develop a set of measurement signals at each of the plurality of source positions. Derivative Radon transform data is directly developing by multiplication of the measurement signals of each set by pre-calculated and stored weight factors. Thereafter, an image of the object is reconstructed using the directly developed Radon derivative data.

10 Claims, 1 Drawing Sheet

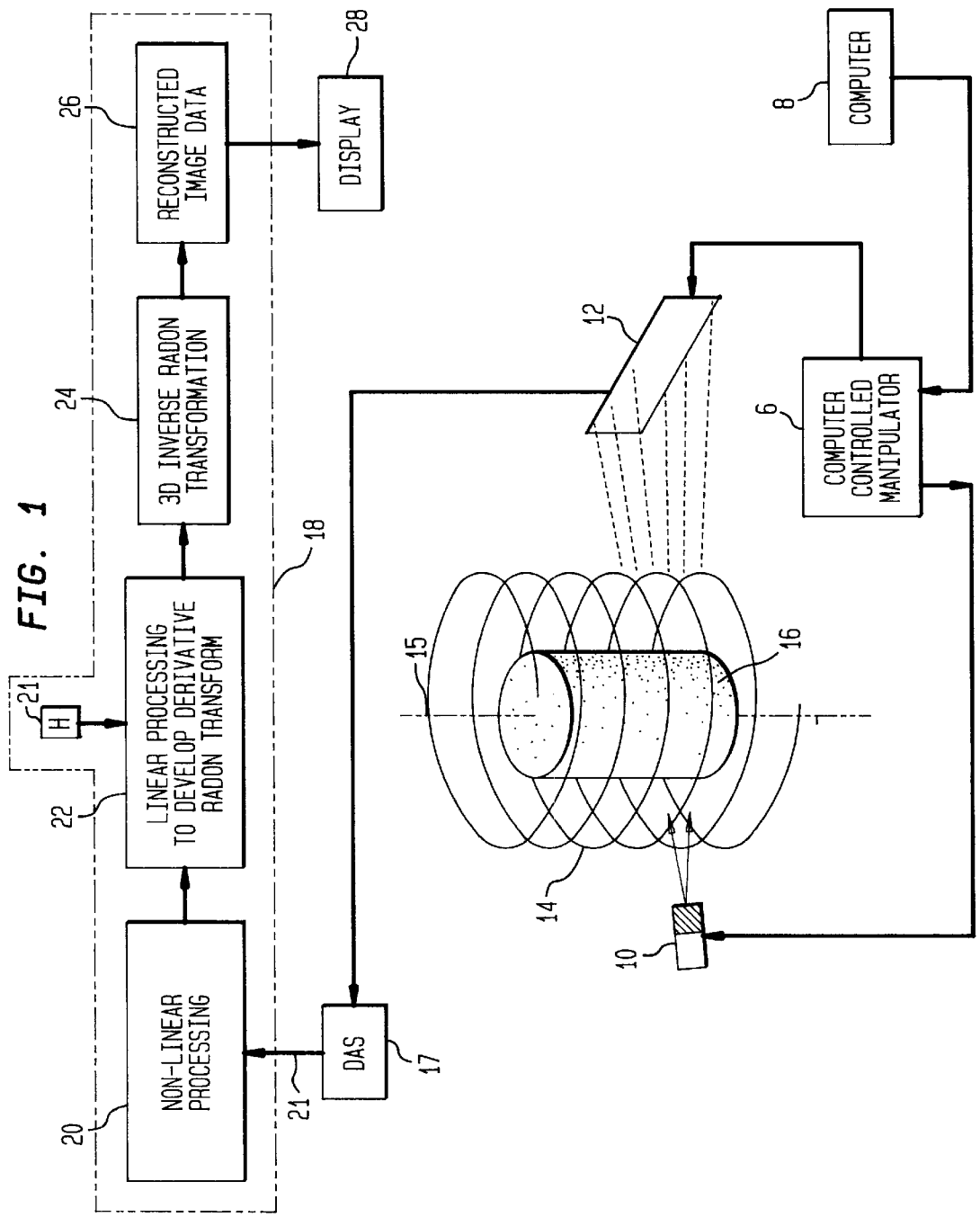

FAST CONE BEAM IMAGE RECONSTRUCTION USING A DETECTOR WEIGHT LIST

BACKGROUND OF THE INVENTION

1. Field of the Invention

The present invention relates generally to computed tomographic (CT) imaging apparatus, and more specifically to a method and apparatus for using a precalculated list of detector element weight factors to greatly improve the computational efficiency of image reconstruction processing performed by a CT imaging apparatus having a cone beam x-ray source.

2. Description of the Background Art

Recently a system employing cone beam geometry has been developed for three-dimensional (3D) computed tomographic (CT) imaging that includes a cone beam x-ray source and a 2D area detector. An object to be imaged is scanned, preferably over a 360° angular range and along its length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sets of cone beam projected measurement data (referred to hereinafter as measurement data), each set of measurement data being representative of x-ray attenuation caused by the object at a respective one of the source positions. After acquisition, the measurement data is processed for reconstructing a 3D image of the object.

As compared with the processing required for reconstructing an image when using an x-ray source supplying parallel or fan beams, the processing of the measurement data acquired when using a cone beam source is computationally much more complex. This is because when using a parallel or fan beam source, the measurement data is already directly representative of a 2D Radon transform of a cross-section of the object. However, this is not the case when using a cone beam source. Processing of the measurement data acquired using a cone beam source comprises:

1) conversion of the measurement data to Radon derivative data. This may be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference, 2) conversion of the Radon derivative data to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference, and 3) performing an inverse 3D Radon transformation of the Radon data using known techniques, such as those described in detail in the forenoted U.S. Pat. No. 5,257,183 for reconstructing image data that, when applied to a display, provides a view of the 3D CT image of the object.

Although the theory for exactly reconstructing an image using cone beam measurement data is generally known, such as from the U.S. patents noted above, a practical implementation of the processing turns out to be quite problematic. Not only is the amount of measurement data to be processed very large and rapidly acquired in accordance with a timing that is mainly determined by the geometry of the scan path, but the calculations required on the acquired data are quite complex. The most computationally expensive part of the object reconstruction is the calculation of the Radon derivative data (step 1 noted above). As noted in the above U.S. patents, as well as in detail in U.S. Pat. No. 5,463,666 entitled HELICAL AND CIRCLE SCAN REGION OF INTEREST COMPUTERIZED TOMOGRAPHY issued Oct. 31, 1995, hereby incorporated by reference, for calculating the value of the Radon data at a given Radon sample point, it is typically necessary to process the measurement data acquired from several source positions, with the measurement data from each source position developing a contribution to the final value for that sample point by way of data combination. Typically one needs to calculate about $100 \cdot 10^6$ line integral derivatives. Each line integral derivative requires the calculation of $200 \cdot 10^6$ single line integrals, since one uses the difference between two closely spaced line integrals to calculate a single line integral derivative. However, before one can perform these line integral derivative calculations, one has to compute for each Radon sample which source positions will provide the measurement data that must be processed, and determine the lines on the measurement data along which the integration must be performed. These latter determinations involve highly non-linear calculations and are therefore computationally costly. In order to compute the contributing source positions, one has to intersect the source scanning path with the Radon integration plane as explained in the forenoted U.S. Pat. No. 5,463,666. When using a spiral scan path, this requires the solution of transcendental equations, which are computationally expensive. Furthermore, in addition to determining the lines on the measurement data along which the integration must be performed, one also has to calculate the appropriate end points of those lines for data combination purposes and region-of-interest masking. The complexity of these above-noted calculations leads to severe bottlenecks in processing of the measurement data, so as to prevent rapid and efficient image reconstruction.

One prior art technique for improving the efficiency of the reconstruction processing is described in a group of patents, of which U.S. Pat. No. 5,559,846 entitled TECHNIQUE FOR IMPROVING PROCESSOR EFFICIENCY IN CT IMAGING is representative.

In accordance with this technique a rather brute force image reconstruction processing method is disclosed wherein a plurality of simultaneously operating parallel processors process the acquired measurement data to develop the Radon transform data.

Another prior art approach is described in the U.S. patent application Ser. No. 08/948,924 of Sauer et al entitled A PRE-CALCULATED HITLIST FOR REDUCING RUN-TIME PROCESSING OF AN EXACT CONE BEAM RECONSTRUCTION ALGORITHM, filed Sep. 30, 1997, wherein before operation of a cone beam imaging apparatus for acquiring and processing the measurement data to reconstruct an image of an object, information required for processing of the acquired measurement data, such as parameters that define the line integrals that need to be calculated, is pre-calculated and stored. The pre-calculated information is then used during the imaging operation of the cone beam apparatus for calculating the line integrals and other processing of the acquired measurement data for reconstructing an image of the object. The pre-calculated image reconstruction information is organized into what is referred to as a "hitlist". In general, the hitlist contains processing information that is determined primarily by geometric parameters of the imaging apparatus that are already predetermined during its imaging operation, such as the pitch and other parameters of the source/detector scan path, the object dimensions, the detector resolution, and a desired sampling of the scan path and the Radon space. In addition to parameters that define the line integrals that need to be calculated, the hitlist includes processing information indicating the correspondence between points in Radon space and the source positions that contribute thereto, as well as other information useful for image reconstruction processing. Once the derivative Radon data is developed, the reconstructed image is provided by integration and inversion of the Radon transform data, as is conventional in the art, or the two-step inversion technique described of Sauer et al entitled TWO-STEP RADON INVERSION PROCESSING FOR PHI-PLANES HAVING LOCAL RADON ORIGINS, filed Sep. 30, 1997 could be used.

Although calculation of the hitlist information is computationally expensive, since the information in the hitlist must be calculated anyway in order to process each set of the acquired measurement data during imaging operation of the apparatus, its pre-calculation provides a very significant speed-up of the run-time (image) processing of the measurement data and results in a greatly improved efficiency in the implementation of the image reconstruction algorithm.

It would be desirable to extend the hitlist concept to its maximum reasonable limit in order to even further minimize the run-time processing of the measurement data, thereby further improving the implementation efficiency of the image reconstruction algorithm.

The present invention is directed to a method and apparatus which extends the hitlist concept to its maximum reasonable limit in the environment of exact cone beam image reconstruction processing.

SUMMARY OF THE INVENTION

In accordance with the principle of the present invention, for each pixel measurement (i.e. for each picture element of the 2-D detector array, at each measurement position of the detector-source assembly), weight factors which determine the contribution of this pixel measurement to samples of the radial derivative of the object's 3-D Radon transform, are pre-calculated and stored. These weight factors essentially represent the point-spread function between the detector space and 3-D Radon space. The pre-calculated pixel weights are organized into what is referred to as a "detector weight list". The pre-calculated weights of the detector weight list are stored in a database which is used during run-time operation of the apparatus for supplying weight factors which are multiplied with corresponding ones of the pixel measurement data so as to simply and quickly develop contributions to the derivative of the Radon transform.

The invention not only provides for a significant speed-up of the processing of the measurement data, but also allows one to increase the precision of the reconstruction, since there are no time constraints for the pre-calculation of the detector weight factors. Furthermore, simple multiprocessor hardware, such as array-processors, can be used for a fast and cost-efficient implementation of the invention. Although the storage requirement for the detector weight list is great, it can become manageable if one uses memory reduction techniques that take advantage of symmetries in the imaging system and/or processing, such as use of the technique of local Radon origins, described in U.S. Ser. No. 08/940,489, filed Sep. 30, 1997, and assigned to the same Assignee as the present patent.

BRIEF DESCRIPTION OF THE DRAWING

The sole FIGURE is a block diagram and simplified perspective illustration of the imaging of an object using a cone beam imaging apparatus, wherein the apparatus uses a pre-calculated and stored list of detector weights for processing acquired measurement data in accordance with the principles of the present invention.

DETAILED DESCRIPTION OF THE PREFERRED EMBODIMENTS

The sole FIGURE illustrates a cone beam 3D CT imaging apparatus that operates in accordance with the principles of the present invention. Except as to be specifically described later with respect to implementation of image reconstruction processing in accordance with the present invention, the illustrated imaging apparatus is constructed and operates substantially the same as described in the forenoted U.S. Pat. Nos. 5,257,183 and 5,446,776.

As shown in the FIGURE, a computer controlled manipulator 6, in response to control signals from an appropriately programmed computer 8, cause a source 10 of a cone beam of energy (such as x-rays) and a two-dimensional pixelated detector array 12 to cooperate (scan) at a plurality of discreet, sequentially occurring adjacent source positions, along a pre-defined source scanning path. In the illustrated embodiment the scanning path is shown as a spiral scan path 14 centered on a predetermined axis 15 of an object 16. As a result of the source/detector cooperation detector 12 acquires complete cone beam measurement data which is then used for reconstructing an image of object 16. Alternatively, and equivalently, object 16 could be rotated and translated to cause scanning by a fixed position source and detector. Furthermore, the scanning can be accomplished in a continuous or stepwise manner, and the spiral path can have equally spaced turns (sometimes referred to as stages), or turns with decreasing pitch at the top and bottom edges of a region of interest of the object. Even furthermore, although source 10 is shown as an x-ray source, other types of imaging energy might be useful, such as neutrons, positrons, etc.

Computer 6, manipulator 8, source 10 and detector 12 cooperate to accomplish scanning of the object in a manner generally well understood by those skilled in this art, i.e., such as described in detail in the forenoted U.S. Pat. No. 5,463,666, and therefore discussion of further details of this portion of the operation of the cone beam imaging apparatus is deemed not necessary.

After the x-ray energy passes through the field of view of the imaging apparatus, measurement signals corresponding to the sensed x-ray energy falling on the elements (pixels) within detector 12 are supplied to a data acquisition system (DAS) 17 which, like the previously described portions of FIG. 1, may operate in a fashion well known to those of ordinary skill in this technology for digitizing and storing of the acquired measurement signals.

The measurement signals from DAS 17 are supplied to a buffer memory and image reconstruction processor 18, which may be a computer programmed to perform various data conversions that process the measurement signals so as to reconstruct an image in accordance with the steps generally illustrated by blocks 20 to 24 within processor 18.

More specifically, at block 20 the measurement signals are subjected to various forms of conventional nonlinear pre-processing steps, such as logarithmic processing for converting the acquired measurement signals into measurement data representative of attenuation, as well as other processing needed to correct the measurement data due to non-uniformities in the imaging system. It is noted that alternatively, the non-linear pre-processing of block 20 can be incorporated into the function of DAS 17, thereby making block 22 the first block of processor 18. At block 22 the non-linearly processed measurement data is processed for calculating the radial derivative of the 3-D Radon transform of the imaged object, or more correctly stated, a sampled version of this function. For brevity, these samples are referred to hereinafter as "Radon samples". Without benefit of the present invention, the processing provided by block 22 is complex and very time consuming, and would be accomplished using the prior art techniques described in the background portion of this application as reconstruction processing steps (1) and (2).

At block 24 the Radon samples are integrated for developing samples of the Radon transform, which are then subjected to inverse 3D Radon transformation processing (as is conventional and well known). A suitable technique for a two-step 3D Radon inversion is known and described, for example, in the forenoted U.S. Pat. No. 5,257,183. Alternatively the two-step 3D Radon inversion technique of U.S. patent application Ser. No. 08/940,324 of Sauer et al, incorporated herein by reference, could be used to reduce the size of the detector weight list, by use of the concept of "local Radon origins". The final result is reconstructed image data representative of the spatial distribution of the 3D object, sampled in a Cartesian coordinate system (x,y,z). The image data developed thereby stored at block 26 and then fed from reconstruction processor 18 to a display 28, which may operate in known fashion, to provide a 3D CT view of object 16.

Except for the determination and use of a detector weight list 21 by block 22 for developing the Radon samples, to be described next, a more detailed description of the blocks of the Figure can be found in the forenoted patents and patent applications.

The present inventors realized that by organizing the image reconstruction processing as shown in the sole FIGURE, the calculations needed at block 22 to develop the Radon samples will only involve linear operations. Hence, at the input to block 22, each measurement datum contributes to a given Radon sample in proportion to its measured value. The corresponding proportionality factor is essentially the weight of the contribution. One can also understood these weights as the point-spread-function from detector/measurement space to the 3-D Radon space. The present inventors also realized that these weights are determined solely by the given geometry of the scanner and detector array, and by the desired sampling of the source path and the Radon space. Consequently, in accordance with the principles of the present invention, these weights are pre-calculated and then stored in a "detector weight list" 21. Consequently, calculation of the Radon samples from the acquired measurement data during the run-time operation of the imaging apparatus is reduced to an accumulation of simple multiplications of measurement data by corresponding weights.

Thus, in accordance with the invention, after the raw measurement signals are (non-linearly) pre-processed, the sampled derivative of the object's Radon transform is calculated at block 22 of processor 18 by accumulating the contributions of the measurement data one after the other. Source position after source position, detector element after detector element, detector weight list 21 is used to look up the target Radon samples and corresponding weights to which each measurement datum contributes, and then the value of each measurement datum is multiplied with the corresponding weight from weight list 21 and the result is added to the value stored for that target Radon sample. Initially, the stored value is set to zero. Consequently, the calculations to be performed by block 22 of processor 18 are reduced to simple and fast-acting multiply and add operations.

It is noted that the processing function of integrating the samples of the Radon derivative before Radon transform inversion is advantageously not included in the function of block 22, since the integration process results in a "smearing" of the measurement datum into many samples of the Radon transform, which would unduly burden the storage requirements of detector weight list 21.

Structure and Size of Detector Weight List

The detector weight list database 21 can be sorted according to the Radon samples or as may be more appropriate in some circumstances, according to the measurement data acquired by the detector elements. In the illustrated embodiment the latter case is considered. For each measurement datum, the list can include several entries. Each entry specifies a "target" Radon sample, i.e. a Radon sample the measurement datum contributes to, and the corresponding weight factor with which it contributes. Thus, the weight factors are essentially a substitute for a sequence of linear processing operations that were conventionally separately performed in the prior art, such as detector mapping (cylindrical to flat), detector masking, linear interpolation, line integration, derivative calculation, etc. The weight list may be ordered according to the source positions (i.e. in the same order the scan path is traversed and the measurement data will be received).

As previously noted, the weight list contains information for each source position. The information, stored for each source position, lists for each detector element, to which Radon samples it contributes and with which weight it does so.

Consequently, let $W\_S_k$ be the block of information stored for source position #k. Then, $W\_S_k$ contains blocks of information $W\_DE_{i,j}$ which relate to the detector elements with indices i,j. Each $W\_DE_{i,j}$ is a list of target Radon samples $R_{l,m,n}$ and weights W. Accordingly, Weight List={$W\_S_k$ | for all source positions $S_k$}

$W\_S_k$={$W\_DE_{i,j}$| for all detector elements i,j}

$W\_DE_{i,j}$={$R_{l,m,n}$, W| for all Radon samples $R_{l,m,n,}$ to which detector element i,j at source position $S_k$ contributes}

Thus, there has been shown and described a novel method and apparatus for greatly speeding up exact image reconstruction processing in a cone beam CT imaging apparatus. Many changes, modifications, variations and other uses and applications of the invention will, however, become apparent to those skilled in the art after considering this specification and its accompanying drawing, which disclose a preferred embodiment thereof. All such changes, modifications, variations and other uses and applications which do not depart from the general teaching of the invention described herein, are deemed to be covered by this patent, which is limited only by the claims which follow, as interpreted in light of the foregoing description.

We claim:

1. A method for three dimensional computerized tomographic imaging of an object, the method comprising the steps of:

applying cone beam energy from a cone beam source to at least a portion of an object to be imaged;

causing relative rotational motion between the source and the object along a path scanning trajectory, said applying step occurring at a plurality of source positions along said path scanning trajectory;

receiving cone beam energy from the source on an area detector comprising a plurality of detector elements arranged in an array of rows and columns, the detector being positioned so as to receive the cone beam energy and develop, via the detector elements, a set of measurement signals at each of said plurality of source positions in response to the detector elements receiving the energy;

pre-processing the sets of measurement signals for developing corresponding sets of measurement data representative of energy attenuation caused by said object during the receipt of said energy;

linear processing of the pre-processed measurement data so as to develop derivative Radon transform data by multiplication of the measurement data of each set by pre-calculated and stored weight factors; and reconstructing an image of the object using said Radon derivative data.

2. The method as recited in claim 1, wherein said linear processing step comprises directly developing by said multiplication, a plurality of additive contributions to said derivative Radon transform data.

3. The method as recited in claim 1, wherein said step of reconstructing an image includes performing an inverse Radon transformation of said derivative Radon data.

4. The method as claimed in claim 2, wherein said step of reconstructing an image includes integration of the derivative Radon data to develop Radon data before performing the inverse Radon transformation.

5. A method for three dimensional computerized tomographic imaging of an object, the method comprising the steps of:

applying cone beam energy from a cone beam source to at least a portion of an object to be imaged by causing relative rotational motion between the source and the object at a plurality of source positions along a path scanning trajectory;

receiving cone beam energy from the source on an area detector comprising a plurality of detector elements arranged in an array of rows and columns, the detector being positioned so as to receive the cone beam energy and develop, via the detector elements, a set of measurement signals at each of said plurality of source positions in response to the detector elements receiving the energy;

applying correction processing to the sets of measurement signals for developing corresponding sets of measurement data representative of energy attenuation caused by said object during the receipt of said energy;

developing derivative Radon transform data by multiplication of the measurement data of each set of measurement data by pre-calculated and stored weight factors; and reconstructing an image of the object using said Radon derivative data.

6. The method as recited in claim 5, wherein said directly developing step comprises directly developing by said multiplication, a plurality of additive contributions to said derivative Radon transform data.

7. Apparatus for three dimensional computerized tomographic imaging of an object, the apparatus comprising:

a source for applying cone beam energy from a cone beam source to at least a portion of the object;

a scanning apparatus for causing relative rotational motion between the source and the object in a path scanning trajectory, said applying step occurring at a plurality of source positions along said path scanning trajectory;

an area detector for receiving cone beam energy from the source on an area detector comprising a plurality of detector elements arranged in an array of rows and columns that is positioned to receive the cone beam energy, and to develop a set of measurement signals in response to the receipt of said energy by the detector elements, at each of said plurality of source positions;

a pre-processor for pre-processing the developed sets of measurement signals for developing sets of measurement data representative of energy attenuation caused by said object during said relative rotational motion;

a database of pre-calculated and stored weight factors;

a linear processor for linear processing of the pre-processed measurement data so as to develop derivative Radon transform data by multiplication of measurement data of each set by precalculated and stored weight factors stored in the database; and a final processor and display apparatus for reconstructing an image of the object using said Radon derivative data.

8. The apparatus as recited in claim 7, wherein said final processor performs an inverse Radon transformation of said derivative Radon data.

9. The apparatus as recited in claim 8, wherein said final processor includes means for integration of the derivative Radon data to develop Radon data before performing the inverse Radon transformation.

10. The apparatus as recited in claim 7, wherein said database is sorted according to the source scanning path positions, and the developed sets of detector element measurement data.

* * * * *